United States Patent [19]

Damani

[11] Patent Number: 5,262,164
[45] Date of Patent: Nov. 16, 1993

[54] SUSTAINED RELEASE COMPOSITIONS FOR TREATING PERIODONTAL DISEASE

[75] Inventor: Nalinkant C. Damani, Cincinnati, Ohio

[73] Assignee: The Procter & Gamble Company, Cincinnati, Ohio

[21] Appl. No.: 439,064

[22] Filed: Nov. 17, 1989

[51] Int. Cl.⁵ .............................................. A61F 13/00
[52] U.S. Cl. .................................. 424/422; 424/434; 424/435; 424/449
[58] Field of Search ................ 424/435, 434, 449, 422

[56] References Cited

U.S. PATENT DOCUMENTS

| | | | |
|---|---|---|---|
| Re. 33,093 | 10/1989 | Schiraldi | 424/435 |
| 2,976,251 | 3/1961 | Brokaw et al. | 252/316 |
| 3,867,190 | 2/1975 | Schmitt et al. | 117/138.8 |
| 4,098,885 | 7/1978 | Curtis | 424/212 |
| 4,175,326 | 11/1979 | Goodson | 424/435 |
| 4,219,548 | 8/1980 | Reller | 424/234 |
| 4,250,163 | 2/1981 | Nagai | 424/434 |
| 4,568,536 | 2/1986 | Kronenthal et al. | 424/22 |
| 4,650,665 | 3/1987 | Kronenthal et al. | 424/435 |
| 4,670,252 | 6/1987 | Sampathkumar | 424/53 |
| 4,764,377 | 8/1988 | Goodson | 424/435 |
| 4,788,062 | 11/1988 | Gale | 424/449 |
| 4,863,970 | 9/1989 | Patel et al. | 514/784 |
| 5,143,934 | 9/1992 | Lading et al. | 514/396 |

Primary Examiner—Thurman K. Page
Assistant Examiner—W. Benston
Attorney, Agent, or Firm—Douglas C. Mohl; Kim William Zerby

[57] ABSTRACT

This invention relates to compositions and methods for treating diseases of the oral cavity in humans and lower animals using a glycerol monooleate gel for releasing drugs in the oral cavity.

12 Claims, No Drawings

SUSTAINED RELEASE COMPOSITIONS FOR TREATING PERIODONTAL DISEASE

TECHNICAL FIELD

This invention relates to compositions for treating diseases of the oral cavity, which compositions are placed in or around the periodontal pocket. The invention also relates to methods of using the compositions in humans and lower animals suffering from such diseases.

Periodontal disease, for example, is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Recent developments in the art are directed toward delivering the therapeutic agent directly to the periodontal pocket, in some cases in a controlled release formulation. Gordon et al. have described the use of a drug-filled polymer hollow fiber. (J.M. Goodson et al., "Periodontal Therapy by Local Delivery of Tetracycline", *J. Clin. Periodontal.* 6, 83 (1979), J. Lindhe et al., "Local Tetracycline Delivery Using Hollow Fiber Devices in Periodontal Therapy", *J. Clin. Periodontal.* 6, 141 (1979) and R.L. Dunn et al., "Monolithic Fibers for Controlled Delivery of Tetracycline", in *Proc. Ninth Int. Symposium on Controlled Release of Bioactive Materials*, Ft. Lauderdale, FL, July (1982). This device is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more. Similar results have been obtained by Coventry and Newman (J. Coventry and H. N. Newman, "Experimental Use of a Slow Release Device Employing Chlorhexidine Gluconate in Areas of Acute Periodontal Inflammation", *J. Clin. Periodontal.* 9, 129 (1982) and Addy et al. (M. Addy et al., "The Development and in vitro Evaluation of Acrylic Strips and Dialysis Tubing for Local Drug Delivery", *J. Periodontal* 53, 693 (1982) using acrylic strips 1 mm or more long, impregnated with chlorhexidine, tetracycline or metronidazole, which were inserted into the periodontal pocket with tweezers. Such a strip, formed from ethylcellulose impregnated with metronidazole, is disclosed by Loesche in U.S. Pat. No. 4,568,538 (February 1986). Another strip, employing a water soluble polymer of a particular elasticity and viscosity, is disclosed by Suzuki et al. in U.S. Pat. No. 4,569,837.

In addition to the above approaches, the prior art also discloses using putty-like compositions containing an antimicrobial for insertion into the periodontal pocket. See U.S. Pat. No. 4,650,665, Mar. 17, 1987 to Kronenthal et al., incorporated herein by reference.

Gel forming materials like hydroxypropyl methyl cellulose or pluronic F-127 polyol have been utilized in the past without success. It has been found that instead of using such hydrophilic or water soluble materials, desirable physical properties, convenience of placement and duration of retention can also be achieved by using materials that have limited water solubility. What is surprising, however, is that some of these materials are capable of absorbing water and undergoing increase in viscosity, providing a most desirable feature to treat disorders of the oral cavity.

The present inventor has discovered that compositions employing glycerol monooleate (monoolein) gels provide for easy placement in and around the periodontal pocket and good drug release.

When a material such as monoolein is compounded with an active agent and placed into or around the periodontal cavity, it absorbs water from the surrounding body fluid and becomes more viscous. Since monoolein is not miscible with water, it provides extended duration of retention at the site of treatment. The active agent is slowly released from the composition in a controlled manner over extended duration.

It is therefore an object of the present invention to provide monoolein compositions suitable for treating diseases of the oral cavity.

It is a further object of the present invention to provide such compositions using monoolein compositions which additionally employ a polymer.

It is still a further object of the present invention to provide a method of treating periodontal disease.

All percentages and ratios used in here are by weight unless otherwise indicated.

All measurements are made at 25° C. unless otherwise indicated.

SUMMARY OF INVENTION

The present invention relates to compositions and methods for treating diseases of the oral cavity by inserting the compositions into or around the periodontal pocket of humans and/or lower animals. The compositions comprise monooleate and an agent providing relief of diseases of the oral cavity.

DETAILED DESCRIPTION OF THE INVENTION

The essential as well as optional components of the compositions of this invention are described below.

Monoolein

The gelling agent useful with the present invention is a monooleate ester of glycerol (monoolein). Monoolein is an item of commerce and is available from C. P. Hall and Co. as CPH-362-N. This agent can easily be formulated with the drug active and be easily positioned into and around the periodontal pocket.

Monoolein comprises the bulk of the compositions of the present invention. The amount employed is generally in the range of from about 1% to about 99%, preferably from about 10% to about 90%, most preferably from about 20% to about 80%.

Drug Active

The drugs useful for use in the present compositions are varied and many and include any agent which provides treatment of diseases of the oral cavity. Some therapeutic agents which are amenable to delivery by this means and are potentially of value for periodontal therapy, include (but are not limited to) antimicrobial agents/antibacterial agents such as iodine, sulfonamides, mercurials, bisbiguanides, or phenolics; antibiotics such as tetracycline, neomycin, kanamycin, metronidazole, or clindamycin; antiinflammatory agents such as aspirin, naproxen, ibuprofen, flurbiprofen, indomethacin, eugenol, or hydrocortisone; immune-suppressive or stimulatory agents such as methotrexate or levamasole; dentinal desensitizing agents such as strontium chloride or sodium fluoride; odor masking agents such as peppermint oil or chlorphyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; or peroxides such as urea peroxide. It is recognized that in certain forms of therapy, combinations of these agents in the same delivery system may be useful in order to obtain an optimal effect. Thus, for example, an antibacterial and an antiinflammatory agent may be combined in a single delivery system to provide combined effectiveness.

The drug active is used at a level of from about 1% to about 90%, preferably from about 5% to about 50% of the compositions.

Compositions can be desirably tailored to provide sustained retention and slow release of one or more actives at the treatment site, by varying the ratios of components and, quantity of the product applied at the treatment site.

Optional Components

In addition to the drug active, the compositions of the present invention may include a variety of optional components. Such components include, but are not limited to, surfactants, viscosity controlling agents, complexing agents, antioxidants, other polymers such as carboxymethyl cellulose, gums such as guar gum, waxes/oils such as castor wax, castor oil, glycerol, dibutyl phthalate and di(2-ethylhexyl phthalate) as well as many others. If used, these optional components comprise from about 0.1% to about 20%, preferably from about 0.5% to about 5% of the total composition.

METHOD OF MANUFACTURE

Methods of manufacturing the compositions of this invention are disclosed in the Examples.

The following Examples further describe and demonstrate the preferred embodiments within the scope of the present invention. The Examples are given solely for the purpose of illustration and are not to be constructed as limitations of the present invention as many variations thereof are possible without departing from its spirit and scope.

EXAMPLE I

The following is an exemplary composition of the present invention.

|  | Weight % |
| --- | --- |
| Tetracycline hydrochloride | 49.9 |
| Hydroxypropyl cellulose | 2.5 |
| Glycerol monooleate | 47.6 |

The above composition can be prepared in a number of different ways. One way is as follows: The monooleate is heated to about 5° C. The hydroxypropyl cellulose is then added in powdered form and dissolved. The drug is added and mixed until uniform. The mixture is then cooled and packaged.

The compositions of the invention of this application are inserted into or around the periodontal pocket or gingival region, and are administered in the form of a gel which sets up. The composition can be put into or around the pocket in any number of ways such as with a syringe.

EXAMPLE II

Given below is another composition of the present invention:

|  | Wt. % |
| --- | --- |
| Clindamycin phosphate | 35 |
| Hydroxypropyl cellulose | 5 |
| Lecithin | 25 |
| Glycerol monooleate | 30 |
| Polyethylene glycol-400 | 5 |

EXAMPLE III

Given below is still another composition representative of the present invention:

|  | Wt. % |
| --- | --- |
| Metronidazole | 30 |
| Hydroxypropyl cellulose | 2 |
| Lecithin | 15 |
| Glycerol monooleate | 53 |

What is claimed is:

1. A composition suitable for insertion into or around the periodontal pocket of a person or lower animal suffering from diseases of the oral cavity consisting essentially of from about 1% to about 99% of monoolein and from about 1% to about 90% of a drug active suitable for treating diseases of the oral cavity selected from the group consisting of antiinflammatory agents, antimicrobials, antibiotics, peroxides, anesthetic agents and vitamins.

2. A composition according to claim 1 wherein the concentration of the drug active is from about 5% to about 50% and the active is selected from the tetracycline group of antibiotics.

3. A composition according to claim 2 which in addition contains another polymer.

4. A composition according to claim 3 wherein the polymer is carboxymethyl cellulose.

5. A method of treating diseases of the oral cavity in a person or lower animal suffering from such disease by placing a composition according to claim 1 into or around the periodontal pocket of said person or lower animal.

6. A method according to claim 5 wherein the composition has a monoolein concentration of from about 20% to about 80%.

7. A method according to claim 6 wherein the drug active is selected from the group consisting of antiinflammatory agents, antibiotics, antimicrobials, peroxides, anesthetic agents, vitamins and mixtures thereof.

8. A method according to claim 7 wherein the drug active is selected from the tetracycline group of antibiotics.

9. A method according to claim 7 wherein said composition additionally contains another polymer.

10. A method according to claim 7 wherein the drug active is an antiinflammatory agent.

11. A method according to claim 7 wherein the drug active is a bisbiguanide compound.

12. A composition suitable for insertion into or around the periodontal pocket of a person or lower animal suffering from diseases of the oral cavity consisting essentially of monoolein, a drug active suitable for treating diseases of the oral cavity, and a wax or oil.

* * * * *

UNITED STATES PATENT OFFICE
CERTIFICATE OF CORRECTION

PATENT NO. : 5,262,164

DATED : November 16, 1993

INVENTOR(S) : Nalinkant Chunilal Damani

It is certified that error appears in the above-identified patent and that said Letters Patent is hereby corrected as shown below:

Column 4, line 3 "$5^\circ$ C" should read -- $50^\circ$ C --.

Signed and Sealed this

Twenty-sixth Day of April, 1994

Attest:

BRUCE LEHMAN

Attesting Officer     Commissioner of Patents and Trademarks